US00PP21950P2

(12) United States Plant Patent
Usami

(10) Patent No.: US PP21,950 P2
(45) Date of Patent: May 31, 2011

(54) ***BEGONIA* PLANT NAMED 'RENAISSANCE EDEN'**

(50) Latin Name: *Begonia×hiemalis*
Varietal Denomination: Renaissance Eden

(75) Inventor: Tatsuo Usami, Aichi (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/658,054

(22) Filed: Feb. 1, 2010

(51) Int. Cl.
*A01H 5/00* (2006.01)

(52) U.S. Cl. ..... Plt./347

(58) Field of Classification Search ..... Plt./347, Plt./346
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'Renaissance Eden', characterized by its upright and mounded plant habit; freely branching habit; leaves with finely-serrated margins; large and showy frilled double flowers with numerous tepals that are yellow and orange in color and are held above and beyond the foliar plane; and excellent postproduction longevity.

1 Drawing Sheet

Botanical designation: *Begonia×hiemalis.*
Cultivar denomination: 'RENAISSANCE EDEN'.

BACKGROUND OF THE INVENTION

The present invention relates to a new and distinct cultivar of *Begonia* plant, botanically known as *Begonia×hiemalis,* commercially known as *Elatior Begonia* and hereinafter referred to by the name 'Renaissance Eden'.

The new *Begonia* plant is a naturally-occurring branch mutation of *Begonia×hiemalis* 'Renaissance Chloris', not patented. The new *Begonia* was discovered and selected by the Inventor on a single flowering plant within a population of plants of 'Renaissance Chloris' in a controlled greenhouse environment in Aichi, Japan in March, 2007.

Asexual reproduction of the new *Begonia* plant by vegetative cuttings taken in a controlled greenhouse environment in Aichi, Japan since August, 2007, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Renaissance Eden'. These characteristics in combination distinguish 'Renaissance Eden' as a new and distinct *Begonia* plant:

1. Upright and mounded plant habit.
2. Freely branching habit.
3. Leaves with finely-serrated margins.
4. Large and showy frilled double flowers with numerous tepals that are yellow and orange in color and are held above and beyond the foliar plane.
5. Excellent postproduction longevity.

Plants of the new *Begonia* differ primarily from plants of the parent, 'Renaissance Chloris', in flower color as plants of 'Renaissance Chloris' have orange-colored flowers. In addition, plants of the new *Begonia* have larger flowers than plants of 'Renaissance Chloris'.

Plants of the new *Begonia* can be compared to plants of *Begonia ×hiemalis* 'Renaissance Flora', not patented. In side-by-side comparisons conducted in Aichi, Japan, plants of the new *Begonia* differed primarily from plants of 'Renaissance Flora' in the following characteristics:

1. Plants of the new *Begonia* were taller than plants of 'Renaissance Flora'.
2. Plants of the new *Begonia* had larger flowers than plants of 'Renaissance Flora'.
3. Plants of the new *Begonia* and 'Renaissance Flora' differed in flower color as plants of 'Renaissance Flora' had orange red-colored flowers.
4. Plants of the new *Begonia* had longer peduncles and pedicels than plants of 'Renaissance Flora'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph at the top of the sheet comprises a side perspective view of a typical flowering plant of 'Renaissance Eden' grown in a container.

The photograph at the bottom of the sheet is a close up view of a typical plant of 'Renaissance Eden'.

DETAILED BOTANICAL DESCRIPTION

The aforementioned photographs and following observations and measurements describe plants grown during the winter in Aichi, Japan, under commercial practice in 15-cm containers in a polyethylene-covered greenhouse. During the production of the plants, the day temperatures ranged from 10° C. to 35° C. and the night temperatures ranged from 15° C. to 25° C. Plants were eight months old when the photographs and description were taken. In the following description, color references are made to The Royal Horticultural Society Colour Chart, 2001 Edition, except where general terms of ordinary dictionary significance are used.

Botanical classification: *Begonia×hiemalis* 'Renaissance Eden'.

Parentage: Naturally-occurring branch mutation of *Begonia×hiemalis* 'Renaissance Chloris', not patented.

Propagation:

*Type.*—By terminal vegetative cuttings.

*Time to develop roots, summer.*—About 25 days at temperatures of 26° C. to 35° C.

*Time to develop roots, winter.*—About 30 days at temperatures of 16° C. to 20° C.

*Time to produce a rooted young plant, summer.*—About 40 days at temperatures of 26° C. to 35° C.

*Time to produce a rooted young plant, winter.*—About 45 days at temperatures of 16° C. to 20° C.

*Root description.*—Fine, fibrous; white in color.

*Rooting habit.*—Freely branching; plants of the new *Begonia* have not been observed to form tubers.

Plant description:

*Plant form and growth habit.*—Upright and mounded plant habit, broad inverted triangle; freely branching with good stem strength; flowers are fully double and positioned above the foliar plane; moderately vigorous growth habit; vegetative shoots are formed at basal nodes and flowering shoots are formed at upper nodes.

*Plant height.*—About 25 cm.

*Plant width.*—About 30 cm.

*Lateral branches.*—Length: About 17.3 cm. Diameter: About 9.6 mm. Internode length: About 1.7 cm. Aspect: Upright to outwardly. Texture: Smooth, glabrous. Color: Close to 144B.

*Leaves.*—Arrangement: Alternate; simple. Fully expanded leaves, length: About 13 cm. Fully expanded leaves, width: About 12 cm. Shape: Roughly reniform, asymmetrical. Apex: Acute. Base: Cordate; asymmetric. Margin: Finely double-serrate. Texture, upper and lower surfaces: Smooth, glabrous. Venation pattern: Palmate. Color: Developing leaves, upper surface: Close to 146B. Developing leaves, lower surface: Close to 146D. Fully expanded leaves, upper surface: Close to 137A; venation, close to N144C. Fully expanded leaves, lower surface: Close to 148B; venation, close to N144C. Petioles: Length: About 5.6 cm. Diameter: About 5 mm. Texture, upper and lower surfaces: Sparsely pubescent. Color, upper and lower surfaces: Close to 144B; towards the base, close to 185B.

Flower description:

*Flowering habit.*—Large frilled double flowers with tepals arranged in axillary cymes; usually three to four flowers per cyme and about 15 cymes per plant; flowers positioned above and beyond the foliar plane.

*Natural flowering season.*—Plants begin flowering about 90 days after planting; plants will flower year round regardless of nyctoperiod, however plants flower earlier, more abundantly and continuously from January until the end of June in Japan; flowers not persistent.

*Fragrance.*—None detected.

*Flowers.*—Shape: Rounded; rose-like. Diameter: About 7 cm. Depth (height): About 3.2 cm.

*Flower buds.*—Length: About 1.8 cm. Diameter: About 1.5 cm. Shape: Globose. Color: Close to 145D; towards the apex, close to 38A.

*Tepals.*—Arrangement: Rosette. Quantity per flower: Numerous, typically about 40 to 160 per flower. Size: Outer tepals, length: About 3.4 cm. Outer tepals, width: About 3.8 cm. Inner tepals, length: About 9 mm to 34 mm. Inner tepals, width: About 2.8 mm to 38 mm. Shape: Rounded to obovate. Apex: Rounded to obtuse. Base: Rounded to obtuse. Margin: Crenate, frilled; undulated. Texture, upper and lower surfaces: Smooth, glabrous. Color, outer tepals: When opening, upper surface: Close to 25A; towards the base, close to 3C. When opening, lower surface: Close to 27D; towards the base, close to 5D. Fully opened, upper surface: Close to 37A; towards the base, close to 2D. Fully opened, lower surface: Close to 37B; towards the base, close to 2D. Color, inner tepals: When opening, upper surface: Close to 5D to 25D; towards the base, close to 3C. When opening, lower surface: Close to 1D to 27A; towards the base, close to 5D. Fully opened, upper surface: Close to 2D to N25A; towards the base, close to 2D. Fully opened, lower surface: Close to 2D to 32C; towards the base, close to 2D.

*Flower bracts.*—Length: About 33.8 mm. Width: About 23.3 mm. Color: Blend of 145B and 141B and 48C and 52A.

*Peduncles.*—Angle: Outwardly. Length: About 6.1 cm. Diameter: About 5 mm. Texture: Pubescent. Color: Close to 144B.

*Pedicels.*—Angle: Outwardly. Length: About 4 cm. Diameter: About 4.2 mm. Texture: Smooth, glabrous. Color: Close to 144B.

*Reproductive organs.*—Stamens: None observed. Pistils: None observed.

*Seed/fruit.*—Seed and fruit production have not been observed as reproductive organs are not formed.

Postproduction longevity: Excellent postproduction longevity, plants last about 150 days.

Disease/pest resistance: Resistance to pathogens and pests common to *Begonia* plants has not been observed.

Temperature tolerance: Plants of the new *Begonia* have been observed to tolerate temperatures from about 15° C. to about 35° C.

It is claimed:

1. A new and distinct *Begonia* plant named 'Renaissance Eden' as illustrated and described.

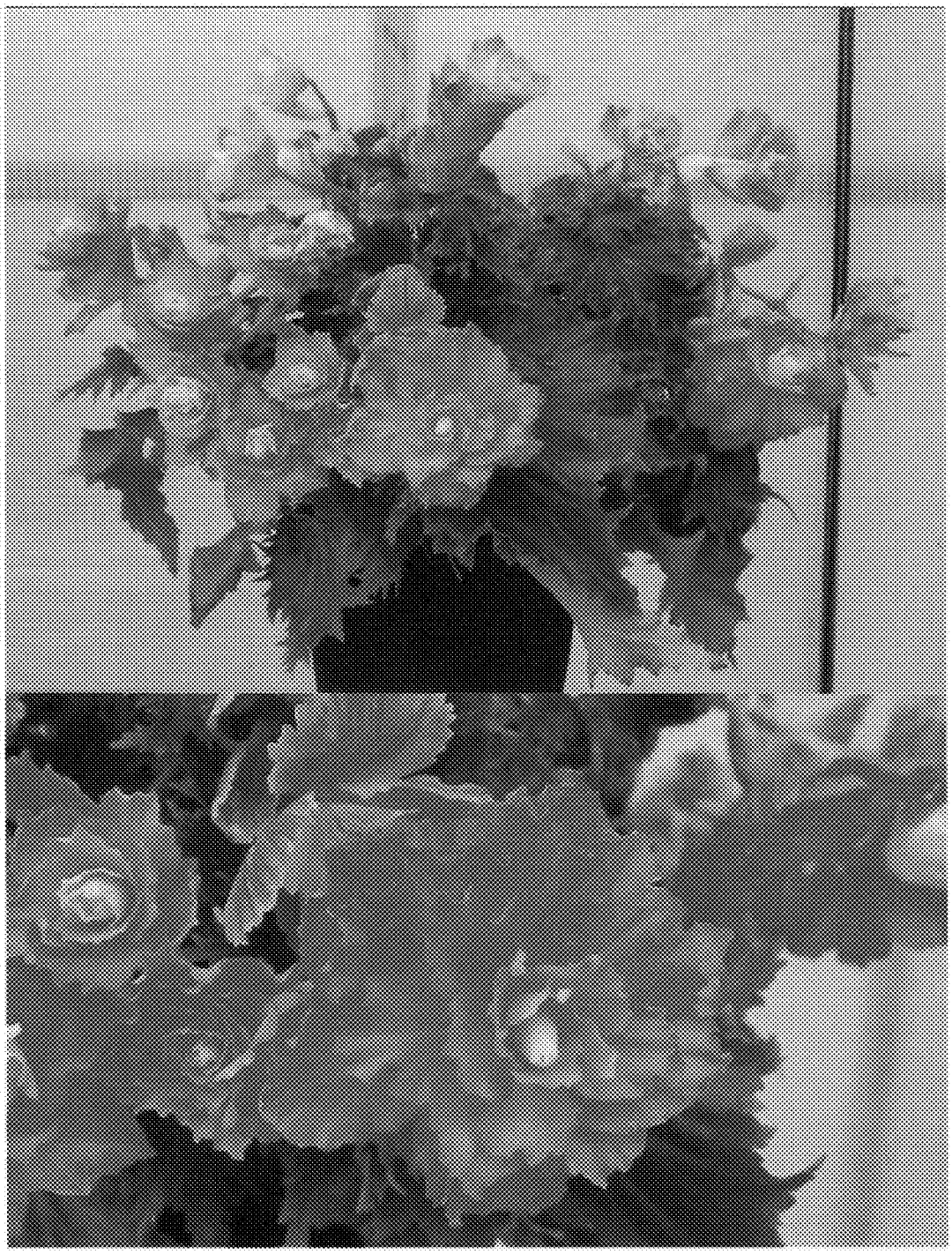

* * * * *